United States Patent
Malek

(10) Patent No.: US 9,492,214 B2
(45) Date of Patent: Nov. 15, 2016

(54) FLEXIBLE SPINAL STABILIZATION SYSTEM

(76) Inventor: Michel H. Malek, Chicago, IL (US)

(*) Notice: Subject to any disclaimer, the term of this patent is extended or adjusted under 35 U.S.C. 154(b) by 1185 days.

(21) Appl. No.: 12/338,319

(22) Filed: Dec. 18, 2008

(65) Prior Publication Data

US 2010/0160964 A1 Jun. 24, 2010

(51) Int. Cl.
| | |
|---|---|
| A61F 2/44 | (2006.01) |
| A61B 17/80 | (2006.01) |
| A61B 17/68 | (2006.01) |
| A61B 17/56 | (2006.01) |
| A61B 17/70 | (2006.01) |
| A61F 2/28 | (2006.01) |
| A61F 2/30 | (2006.01) |

(52) U.S. Cl.
CPC ......... *A61B 17/8085* (2013.01); *A61F 2/4455* (2013.01); *A61B 17/68* (2013.01); *A61B 17/70* (2013.01); *A61B 17/7061* (2013.01); *A61B 2017/561* (2013.01); *A61B 2017/564* (2013.01); *A61F 2/44* (2013.01); *A61F 2002/2821* (2013.01); *A61F 2002/2835* (2013.01); *A61F 2002/30576* (2013.01); *A61F 2002/449* (2013.01); *A61F 2002/4415* (2013.01); *A61F 2002/4495* (2013.01); *A61F 2310/00017* (2013.01); *A61F 2310/00023* (2013.01); *A61F 2310/00029* (2013.01)

(58) Field of Classification Search
CPC .................................................. A61F 2/4455
USPC ........................................................ 606/280
See application file for complete search history.

(56) References Cited

U.S. PATENT DOCUMENTS

| | | |
|---|---|---|
| 4,011,602 A | 3/1977 | Rybicki et al. |
| 4,349,921 A | 9/1982 | Kuntz |
| 4,401,112 A | 8/1983 | Resaian |
| 4,643,178 A | 2/1987 | Nastari et al. |
| 4,657,550 A | 4/1987 | Daher |
| 4,743,256 A | 5/1988 | Brantigan |
| 4,743,260 A | 5/1988 | Burton |
| 4,759,766 A | 7/1988 | Büettner-Janz et al. |
| 4,759,769 A | 7/1988 | Hedman et al. |
| 4,863,476 A | 9/1989 | Shepperd |
| 4,946,378 A | 8/1990 | Hirayama et al. |
| 4,946,458 A | 8/1990 | Harms et al. |
| 4,997,432 A | 3/1991 | Keller |

(Continued)

FOREIGN PATENT DOCUMENTS

| | | |
|---|---|---|
| DE | 22 63 842 A | 7/1974 |
| DE | 30 23 353 A1 | 4/1981 |

(Continued)

OTHER PUBLICATIONS

The International Search Report and Written Opinion for PCT/US2004/032116 mailed on Feb. 16, 2005, 12 pages.

(Continued)

*Primary Examiner* — Jacqueline Woznicki
(74) *Attorney, Agent, or Firm* — Foley & Lardner LLP

(57) ABSTRACT

Flexible spinal stabilization apparatuses are provided. The apparatuses include a flexible support element configured to be attached to a first vertebra and a second vertebra. The apparatuses also include a bone growth promoter coupled to the flexible support element. The flexible support element spans one or more intervertebral spaces but the bone growth promoter does not.

16 Claims, 3 Drawing Sheets

(56) References Cited

U.S. PATENT DOCUMENTS

| | | |
|---|---|---|
| 5,024,670 A | 6/1991 | Smith et al. |
| 5,084,048 A | 1/1992 | Jacob et al. |
| 5,092,866 A | 3/1992 | Breard et al. |
| 5,122,130 A | 6/1992 | Keller |
| 5,246,458 A | 9/1993 | Graham |
| 5,258,031 A | 11/1993 | Salib et al. |
| 5,261,911 A | 11/1993 | Carl |
| 5,282,863 A | 2/1994 | Burton |
| 5,306,310 A | 4/1994 | Siebels |
| 5,314,477 A | 5/1994 | Marnay |
| 5,314,478 A | 5/1994 | Oka et al. |
| 5,336,223 A | 8/1994 | Rogers |
| 5,352,224 A | 10/1994 | Westermann |
| 5,375,823 A | 12/1994 | Navas |
| 5,380,324 A | 1/1995 | Müller et al. |
| 5,380,328 A | 1/1995 | Morgan |
| 5,401,269 A | 3/1995 | Büttner-Janz et al. |
| 5,415,659 A | 5/1995 | Lee et al. |
| 5,437,671 A | 8/1995 | Lozier et al. |
| 5,458,641 A | 10/1995 | Ramirez Jimenez |
| 5,496,318 A | 3/1996 | Howland et al. |
| 5,534,029 A | 7/1996 | Shima |
| 5,536,124 A | 7/1996 | Silva |
| 5,540,688 A | 7/1996 | Navas |
| 5,556,431 A | 9/1996 | Büttner-Janz |
| 5,562,738 A | 10/1996 | Boyd et al. |
| 5,591,166 A | 1/1997 | Bernhardt et al. |
| 5,607,425 A | 3/1997 | Rogozinski |
| 5,628,740 A | 5/1997 | Mullane |
| 5,645,596 A | 7/1997 | Kim et al. |
| 5,649,925 A | 7/1997 | Barbera Alacreu |
| 5,672,175 A | 9/1997 | Martin |
| 5,688,275 A | 11/1997 | Koros et al. |
| 5,702,453 A | 12/1997 | Rabbe et al. |
| 5,702,455 A | 12/1997 | Saggar |
| 5,713,899 A | 2/1998 | Marnay et al. |
| 5,725,582 A | 3/1998 | Bevan et al. |
| 5,776,198 A | 7/1998 | Rabbe et al. |
| 5,836,948 A | 11/1998 | Zucherman et al. |
| 5,888,226 A | 3/1999 | Rogozinski |
| 5,893,889 A | 4/1999 | Harrington |
| 5,951,553 A | 9/1999 | Betz et al. |
| 5,989,290 A | 11/1999 | Biedermann et al. |
| 6,019,792 A | 2/2000 | Cauthen |
| 6,030,389 A | 2/2000 | Wagner et al. |
| 6,063,121 A | 5/2000 | Xavier et al. |
| 6,074,390 A | 6/2000 | Zucherman et al. |
| 6,083,224 A | 7/2000 | Gertzbein et al. |
| 6,113,637 A | 9/2000 | Gill et al. |
| 6,139,579 A | 10/2000 | Steffee et al. |
| 6,146,420 A * | 11/2000 | McKay ................... 623/17.16 |
| 6,146,421 A | 11/2000 | Gordon et al. |
| 6,179,874 B1 | 1/2001 | Cauthen |
| 6,214,012 B1 | 4/2001 | Karpman et al. |
| 6,217,578 B1 | 4/2001 | Crozet et al. |
| 6,228,118 B1 | 5/2001 | Gordon |
| 6,241,730 B1 | 6/2001 | Alby |
| 6,293,949 B1 | 9/2001 | Justis et al. |
| 6,296,644 B1 | 10/2001 | Saurat et al. |
| 6,296,664 B1 | 10/2001 | Middleton |
| 6,315,797 B1 | 11/2001 | Middleton |
| 6,368,350 B1 | 4/2002 | Erickson et al. |
| 6,375,682 B1 | 4/2002 | Fleischmann et al. |
| 6,375,683 B1 | 4/2002 | Crozet et al. |
| 6,395,034 B1 | 5/2002 | Suddaby |
| 6,402,750 B1 | 6/2002 | Atkinson et al. |
| 6,419,703 B1 | 7/2002 | Fallin et al. |
| 6,454,807 B1 | 9/2002 | Jackson |
| 6,478,800 B1 | 11/2002 | Fraser et al. |
| 6,500,178 B2 | 12/2002 | Zucherman et al. |
| 6,517,580 B1 | 2/2003 | Ramadan et al. |
| 6,520,990 B1 | 2/2003 | Ray |
| 6,540,785 B1 | 4/2003 | Gill et al. |
| 6,554,831 B1 | 4/2003 | Rivard et al. |
| 6,562,073 B2 * | 5/2003 | Foley ..................... A61F 2/446 623/17.11 |
| 6,565,605 B2 | 5/2003 | Goble et al. |
| 6,576,017 B2 * | 6/2003 | Foley ..................... A61F 2/446 623/17.16 |
| 6,579,319 B2 | 6/2003 | Goble et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,585,769 B1 | 7/2003 | Muhanna et al. |
| 6,607,558 B2 | 8/2003 | Kuras |
| 6,616,669 B2 | 9/2003 | Ogilvie et al. |
| 6,626,905 B1 | 9/2003 | Schmiel et al. |
| 6,626,908 B2 | 9/2003 | Cooper et al. |
| 6,652,585 B2 | 11/2003 | Lange |
| 6,685,742 B1 | 2/2004 | Jackson |
| 6,695,842 B2 | 2/2004 | Zucherman et al. |
| 6,730,126 B2 | 5/2004 | Boehm et al. |
| 6,752,831 B2 | 6/2004 | Sybert et al. |
| 6,761,720 B1 | 7/2004 | Senegas |
| 6,764,515 B2 | 7/2004 | Ralph et al. |
| 6,835,205 B2 | 12/2004 | Atkinson et al. |
| 6,852,128 B2 | 2/2005 | Lange |
| 6,902,566 B2 | 6/2005 | Zucherman et al. |
| 6,946,000 B2 | 9/2005 | Senegas et al. |
| 6,966,910 B2 | 11/2005 | Ritland |
| 6,966,931 B2 | 11/2005 | Huang |
| 6,986,771 B2 * | 1/2006 | Paul et al. ..................... 606/254 |
| 6,989,011 B2 | 1/2006 | Paul et al. |
| 7,022,138 B2 | 4/2006 | Mashburn |
| 7,025,787 B2 | 4/2006 | Bryan et al. |
| 7,041,138 B2 | 5/2006 | Lange |
| 7,044,970 B2 | 5/2006 | Errico et al. |
| 7,052,497 B2 * | 5/2006 | Sherman et al. .............. 606/279 |
| 7,056,343 B2 | 6/2006 | Schafer et al. |
| 7,101,375 B2 | 9/2006 | Zucherman et al. |
| 7,147,665 B1 | 12/2006 | Bryan et al. |
| 7,175,623 B2 | 2/2007 | Thramann et al. |
| 7,186,256 B2 | 3/2007 | Michelson |
| 7,201,751 B2 | 4/2007 | Zucherman et al. |
| 7,255,713 B2 | 8/2007 | Malek |
| 7,282,064 B2 | 10/2007 | Chin |
| 7,318,825 B2 | 1/2008 | Butler et al. |
| 7,341,601 B2 * | 3/2008 | Eisermann ............. A61B 17/68 623/17.11 |
| 7,402,176 B2 | 7/2008 | Malek |
| 2001/0001129 A1 * | 5/2001 | McKay et al. ............. 623/17.16 |
| 2001/0016773 A1 | 8/2001 | Serhan et al. |
| 2001/0029375 A1 | 10/2001 | Betz et al. |
| 2001/0032020 A1 | 10/2001 | Besselink |
| 2001/0037111 A1 | 11/2001 | Dixon et al. |
| 2001/0051829 A1 | 12/2001 | Middleton |
| 2002/0022888 A1 | 2/2002 | Serhan et al. |
| 2002/0107574 A1 | 8/2002 | Boehm et al. |
| 2002/0111683 A1 | 8/2002 | Ralph et al. |
| 2002/0147454 A1 | 10/2002 | Neto |
| 2003/0009223 A1 | 1/2003 | Fehling et al. |
| 2003/0009226 A1 | 1/2003 | Graf |
| 2003/0018390 A1 | 1/2003 | Husson |
| 2003/0023312 A1 | 1/2003 | Thalgott |
| 2003/0032958 A1 | 2/2003 | Soubeiran |
| 2003/0055427 A1 | 3/2003 | Graf |
| 2003/0069642 A1 * | 4/2003 | Ralph et al. ............... 623/17.13 |
| 2003/0100951 A1 | 5/2003 | Serhan et al. |
| 2003/0176861 A1 | 9/2003 | Reed |
| 2003/0191534 A1 | 10/2003 | Viart et al. |
| 2003/0229348 A1 | 12/2003 | Sevrain |
| 2004/0002762 A1 | 1/2004 | Hawkins |
| 2004/0153156 A1 | 8/2004 | Cohen et al. |
| 2004/0167626 A1 | 8/2004 | Geremakis et al. |
| 2004/0215192 A1 * | 10/2004 | Justis et al. ..................... 606/61 |
| 2005/0085910 A1 | 4/2005 | Sweeney |
| 2005/0113927 A1 | 5/2005 | Malek |
| 2005/0143823 A1 | 6/2005 | Boyd et al. |
| 2005/0165486 A1 | 7/2005 | Trieu |

(56) References Cited

U.S. PATENT DOCUMENTS

| | | |
|---|---|---|
| 2005/0192675 A1* | 9/2005 | Robinson .................. 623/23.46 |
| 2005/0209593 A1 | 9/2005 | Kolb |
| 2005/0209697 A1 | 9/2005 | Paponneau et al. |
| 2005/0234425 A1 | 10/2005 | Miller et al. |
| 2006/0036243 A1 | 2/2006 | Sasso et al. |
| 2006/0079895 A1 | 4/2006 | McLeer |
| 2006/0095134 A1* | 5/2006 | Trieu et al. ................ 623/17.16 |
| 2006/0106381 A1 | 5/2006 | Ferree et al. |
| 2006/0161154 A1 | 7/2006 | McAfee |
| 2006/0200140 A1 | 9/2006 | Lange |
| 2006/0224223 A1 | 10/2006 | Podhajsky et al. |
| 2007/0010813 A1 | 1/2007 | Zucherman et al. |
| 2007/0112299 A1 | 5/2007 | Smit et al. |
| 2007/0173937 A1 | 7/2007 | Khalili |
| 2007/0191837 A1* | 8/2007 | Trieu .............................. 606/61 |
| 2007/0270828 A1 | 11/2007 | Bruneau et al. |
| 2008/0027444 A1 | 1/2008 | Malek |
| 2009/0048675 A1* | 2/2009 | Bhatnagar .......... A61B 17/0642 623/17.16 |
| 2009/0062919 A1 | 3/2009 | Malek |
| 2009/0177233 A1 | 7/2009 | Malek |
| 2009/0204149 A1 | 8/2009 | Malek |
| 2009/0287118 A1 | 11/2009 | Malek |
| 2010/0121378 A1 | 5/2010 | Malek |
| 2010/0160964 A1 | 6/2010 | Malek |

FOREIGN PATENT DOCUMENTS

| | | |
|---|---|---|
| EP | 0 176 728 A | 4/1986 |
| EP | 0 560 140 B1 | 9/1993 |
| EP | 0 560 141 A | 9/1993 |
| EP | 0 566 810 B1 | 10/1993 |
| FR | 2 694 882 A | 2/1994 |
| FR | 2 801 782 | 6/2001 |
| FR | 2 805 985 | 9/2001 |
| WO | WO 94/04100 | 3/1994 |
| WO | WO 95/26697 | 10/1995 |
| WO | WO 01/06939 | 2/2001 |
| WO | WO 02/24087 | 3/2002 |
| WO | WO 03/094699 | 11/2003 |
| WO | WO 2008/014337 | 1/2008 |
| WO | WO 2009/088746 | 7/2009 |
| WO | WO 2009/100117 | 8/2009 |

OTHER PUBLICATIONS

"Anatomic Facet Replacement System (AFRS™)," *Natural Motion*; published by Facet Solutions, Inc.; http://www.facetsolutions.com/Device.html on or before Nov. 2, 2007, 1 page.

European Patent Office Search Report for Application No. 04812086.9, dated Aug. 19, 2011, 5 pages.

\* cited by examiner

FLEXIBLE SPINAL STABILIZATION SYSTEM

FIELD OF THE INVENTION

The invention generally relates to apparatuses for stabilizing the spine. More specifically, apparatuses are disclosed which are capable of stabilizing the motion of a vertebra relative to another vertebra, without greatly restricting the natural flexion, extension, rotation, lateral bending, axial movement and translation of the spine. The apparatuses are also capable of being integrated into the vertebrae to which they are attached by means of a bone growth promoter coupled to the apparatus.

BACKGROUND

The human spine comprises individual vertebrae that interlock with each other to form a spinal column. Together, two adjacent vertebrae, their facet joints, the intervertebral disc and the connecting ligament tissue make up a motion segment unit, the smallest portion of the spine that exhibits kinematic behavior characteristic of the entire spine. The motion segment unit is capable of flexion, extension, rotation, lateral bending and translation and each component of the unit contributes to the mechanical stability of the entire unit. Trauma, degeneration, aging, disease, surgery, and the like may damage any of the components of the motion segment unit, leading to instability in the unit and causing severe pain, numbness, decreased mobility, muscle weakness and nerve damage to the patient.

One approach to treating these spinal conditions involves the use of spinal devices to stabilize and restrict, but not necessarily eliminate, the relative movement of adjacent vertebra. Spinal devices may include rigid bars, rods, plates, or combinations thereof connecting two sides of a vertebra, the adjacent vertebrae of a motion segment unit, or both. As used herein, such devices will be referred to as spinal devices or conventional spinal devices. Although these spinal devices can preserve some mobility of the motion segment units, they impart a substantial amount of rigidity to the spine. In some cases, they greatly restrict and may even eliminate certain types of motion (e.g., flexion, extension, rotation, lateral bending, axial, translation, etc.).

Another approach to treating spinal conditions involves spinal fusion. In spinal fusion, two or more adjacent vertebrae are permanently fused by forming a bony bridge between the vertebrae in order to stabilize and immobilize the motion segment unit. Ligaments, bone, disc, or combinations thereof may be removed prior to fusion. Spinal devices may be used in combination with spinal fusion to facilitate fusion of the vertebrae. As used herein, spinal devices that facilitate fusion of vertebrae are referred to as spinal fusion devices. By placing the adjacent vertebrae in their nominal position and fusing them in place, the relative movement of the vertebrae is eliminated. Thus, a fused motion segment unit is unable to undergo flexion, extension, rotation, lateral bending, axial and/or translation.

Problems are associated with either approach. The stabilization afforded by conventional spinal devices may be short-lived, since the components of the devices may fail over time. For example, any screws, pins, or hooks attaching the device to the vertebrae may eventually come loose. Another problem associated with both approaches, especially spinal fusion, involves the accelerated degeneration of vertebrae and vertebral discs neighboring the stabilized and/or fused motion segment unit. As described above, conventional spinal devices and spinal fusion devices either eliminate or greatly reduce the mobility of one or more motion segment units. As a result, vertebrae and intervertebral discs neighboring the fused or stabilized motion segment unit must accommodate an even greater degree of motion. This added stress can lead to degeneration of the neighboring vertebrae and intervertebral discs.

SUMMARY

Apparatuses for stabilizing the motion of a vertebra relative to another vertebra and methods for using the apparatuses are provided herein. The apparatuses are capable of stabilizing the motion of a vertebra relative to another vertebra, without greatly restricting the natural flexion, extension, rotation, lateral bending, axial, and translation of the spine. Thus, when used as stand-alone devices, the disclosed apparatuses preserve a greater range of natural motion than do conventional spinal devices or spinal fusion devices. As a result, the problem of accelerated degeneration described above is minimized. In addition, the disclosed apparatuses are capable of becoming integrated into the vertebrae to which they are attached, thereby providing for much longer-term stabilization than conventional spinal devices. Finally, when used in combination with conventional spinal devices or spinal fusion devices, the disclosed apparatuses are capable of protecting vertebrae and intervertebral discs from the increased stress and accelerated degeneration induced by neighboring fused or stabilized vertebrae.

The apparatuses include a flexible support element configured to be attached to a first vertebra and a second vertebra. The flexible support element spans one or more intervertebral spaces. The flexible support element may be formed from a variety of materials, including biocompatible materials. Similarly, the flexible support element may assume a variety of forms. By way of example only, the flexible support element may take the form of a perforated plate having a plurality of apertures. The apertures may be approximately uniformly sized and spaced so that the perforated plate comprises a mesh-type structure.

The apparatuses further include a bone growth promoter coupled to the flexible support element. Unlike the flexible support element, the bone growth promoter does not span one or more intervertebral spaces. A variety of bone growth promoters may be used, including, but not limited to bone morphogenetic protein. The coupling of the bone growth promoter to the flexible support element may be accomplished in a variety of ways, including coating, depositing, or patterning the bone growth promoter onto, or impregnating the bone growth promoter into, the flexible support element. The apparatuses may include a separate compartment coupled to the flexible support element, the compartment containing the bone growth promoter.

The apparatuses may further include a spinal device or a spinal fusion device coupled to the flexible support element. The forms of the devices and the materials used to form the devices may vary. Similarly, the position of devices with respect to the apparatuses and the coupling of the devices to the apparatuses may vary.

Also disclosed are methods for using the apparatuses.

DETAILED DESCRIPTION

Figure 1:
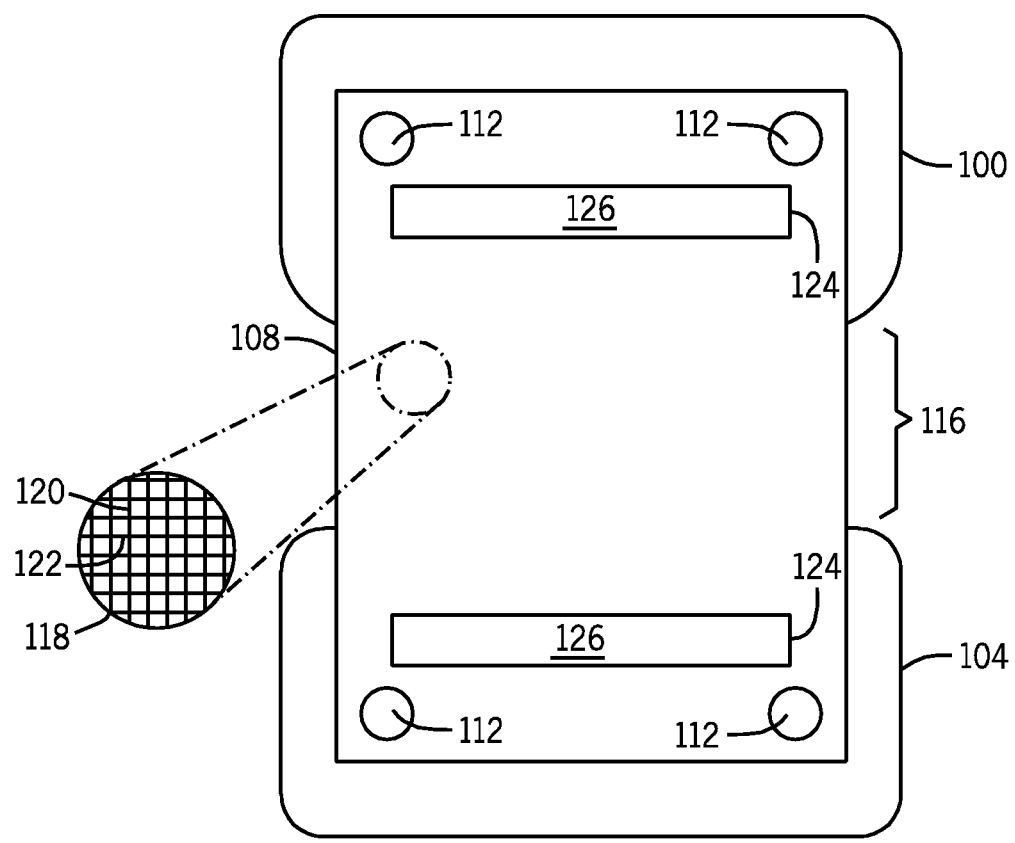
FIG. 1 shows an apparatus including a flexible support element attached to two adjacent vertebrae. Two compartments including a bone growth promoter are coupled to the flexible support element. The flexible support element has a mesh-type structure.

Apparatuses for stabilizing the motion of a vertebra relative to another vertebra and methods for using the apparatuses are provided herein. The apparatuses allow for a broad range of physiologic motion of vertebrae, while providing enough support to protect the vertebrae from excessive movement.

The apparatuses comprise a flexible support element configured to be attached to a first vertebra and a second vertebra. The first and second vertebrae may be adjacent or one or more vertebrae may be disposed between the first and second vertebrae. When implanted, the flexible support element spans one or more intervertebral spaces. By intervertebral space it is meant the space between adjacent vertebrae, a space that is normally occupied by the intervertebral disc. By spanning an intervertebral space, it is meant that the flexible support element extends across the intervertebral space. The flexible support element will typically be attached at the posterior of the spine, but other placements including lateral and anterior placements are also possible.

The first vertebra, the second vertebra, or both may be fused or stabilized vertebrae. By stabilized vertebra, it is meant that the vertebra is also attached to a spinal device that serves to stabilize and restrict, but not necessarily eliminate, the movement of the vertebra relative to one or more other vertebrae. Such conventional spinal devices are further discussed below. By fused vertebra, it is meant that the vertebra is fused to one or more other vertebrae. This fused vertebra may also be attached to a spinal fusion device. In other embodiments, the first vertebra, the second vertebra, or both are non-fused and non-stabilized vertebrae. In yet other embodiments, the first and second vertebra are adjacent vertebrae and the first vertebra is not fused to the second vertebra. However, even in this embodiment, the first and second vertebrae may be fused to other vertebrae.

The materials used to form the flexible support element may vary, provided the material can form a support element that is sufficiently flexible to retain at least some of each of the following motions: flexion, extension, rotation, lateral bending, axial, and translation. In some embodiments, the flexible support element comprises a biologically compatible material. A variety of biologically compatible materials may be used, including, but not limited to, titanium, a titanium alloy, cobalt chrome, a cobalt chrome alloy, ceramics, stainless steel, and a polymer. Non-limiting examples of suitable ceramics include hydroxapatites. Non-limiting examples of polymers include polyethylene, ultrahigh molecular weight polyethylene, and polyether ester ketone. Biologically compatible materials obtained from human and animal tissues, plants and insects such as those described in U.S. Pat. No. 6,752,831 may also be used. The flexible element may also comprise a biocompatible memory metal alloy that exhibits super-elastic properties at body temperature such as disclosed in U.S. Patent Publication No. 2003/0009223.

Similarly, the form of the flexible support element may vary. In some embodiments, flexible support element comprises a perforated plate, the perforated plate comprising a plurality of apertures. The apertures can impart an amount of flexibility to an otherwise rigid plate. The size, shape, and number of apertures may be varied to impart the desired amount of flexibility to the plate. The exact size, shape, and number of the apertures are not critical provided the resulting perforated plate is sufficiently flexible to retain at least some of each of the following motions: flexion, extension, rotation, lateral bending, axial, and translation.

In some embodiments, the apertures are approximately uniformly sized and spaced so that the perforated plate comprises a mesh-type structure. Again, the size and spacing of the apertures in the mesh-type structure are not critical, provided the mesh-type structure is sufficiently flexible to retain at least some of each of the motions described above. In some embodiments, the mesh-type structure is sufficiently flexible so that the structure does not resist the extension, lateral bending, and rotational motion of the spine. The mesh-type structure may be formed from a number of vertical and horizontal components that are woven together in such a way to provide a set of approximately uniformly sized and spaced apertures. By vertical component, it is meant a component that runs approximately parallel to the longitudinal axis of the flexible support element. By horizontal component, it is meant a component that runs approximately perpendicular to the longitudinal axis of the flexible support element. In some embodiments, the mesh-type structure comprises vertical and horizontal components. In some embodiments, the mesh-type structure does not include any diagonal components. By diagonal component, it is meant a component that forms an angle with the longitudinal axis of the flexible support element that is greater than about 0 degrees and less than 90 degrees.

The apparatuses further comprise a bone growth promoter coupled to the flexible support element. By bone growth promoter, it is meant a compound, a composition, or device that is capable of promoting the growth of bone. A variety of bone growth promoters may be used, including, but not limited to bone, demineralized bone matrix, mineralizing proteins, ossifying proteins, bone morphogenetic protein (BMP), hydroxyapatite, or hydroxyapatite tricalcium phosphate. In some embodiments, the bone growth promoter is BMP. An electrical stimulator is another example of a bone growth promoter. Electrical bone growth stimulators are known. The bone growth promoter facilitates the growth of bone over at least a portion of the apparatus, thereby integrating the apparatus into, and anchoring the apparatus to, one or more of the vertebrae to which it is attached. This integration of the apparatus provides for long-term stabilization of the vertebrae and spine. However, unlike the flexible support element, the bone growth promoter does not span the one or more intervertebral spaces. Thus, the bone growth promoter does not facilitate the fusion of, or the growth of bone between, two vertebrae.

The bone growth promoter may be coupled to the flexible support element by a variety of ways, provided the bone growth promoter does not span the one or more intervertebral spaces. In some embodiments, the bone growth promoter is coated or deposited onto the flexible support element. The bone growth promoter may be coated or deposited onto the flexible support element in specific areas or patterns on the flexible support element. In other embodiments, the bone growth promoter is impregnated into the plate. By way of example only, an impregnated polymeric flexible support element may be formed by dispersing the bone growth stimulator into the polymer prior to forming the flexible support element.

In yet other embodiments, the apparatuses comprise a compartment coupled to the flexible support element and the compartment comprises the bone growth promoter. By way of example only, a sponge may be soaked with the bone growth promoter and the sponge inserted into the compartment. The compartment may be coupled to the flexible support element by a variety of ways. In some embodiments, the compartment is a separate compartment attached to the plate by any of the connectors described below. In other embodiments, the compartment is an integral piece of the flexible support element. The size and shape of the compartment are not critical, and may depend upon any of the considerations for the size and shape of the flexible support element itself, as described below. The placement of the compartment on the flexible support element is not critical. In some embodiments, the compartment is positioned so that once implanted, the compartment is sufficiently near the vertebra to facilitate the growth of bone between the flexible support element and the vertebra.

The apparatus may further comprise one or more connectors configured to attach the flexible support element to the first vertebra, the second vertebra, or both. A variety of connectors may be used. Non-limiting examples of connectors are screws, hooks or pins. Suitable screws and hooks include, but are not limited to, pedicle screws, polyaxial pedicle screws, lateral mass screws or polyaxial hooks and the like, such as those disclosed in U.S. Pat. Nos. 5,591,166, 5,628,740, 6,626,908 and U.S. Patent Publication No. 2005/0113927. When attached to a vertebra, the connector may attach to a variety of vertebral elements, including, but not limited to, pedicles, lamina or spinous processes. The placement of the connectors relative to the flexible support element is not critical.

The materials used to form the connectors may vary. The connector may comprise a variety of biocompatible materials, including, but not limited to any of the biocompatible materials disclosed above. The one or more connectors may further comprise a bone growth promoter. The connectors may be coated or impregnated with the bone growth promoter as described above. Any of the bone growth promoters disclosed above may be used.

The dimensions of the flexible support element may vary, depending on such considerations such as minimizing interference with components of the spinal column, ensuring the flexible support element is easily implantable, and providing a strong and durable structure. Similarly, the dimensions of the connectors may vary, provided they are small enough to minimize interference with the components of the spinal column but large enough to secure the flexible support element to the vertebrae.

The apparatuses may further comprise a spinal device coupled to the flexible support element. In some embodiments, the spinal device is a spinal fusion device. Spinal devices and spinal fusion devices are known. In general, the spinal device or spinal fusion device is configured to be attached to one or more vertebrae and includes a support element that spans one or more intervertebral spaces. A variety of support elements may be used, including, but not limited to bars, plates, or rods. The support element may be rigid. The support elements are typically located at the posterior of the spine, but other placement including lateral and anterior placements are also possible. Materials for the devices include, but are not limited to titanium, titanium alloys, cobalt chrome, cobalt chrome alloys, ceramics, and stainless steel. The devices may include any of the connectors described above.

The position of the spinal device or spinal fusion device relative to the flexible support element and the means of coupling the devices to the flexible support element may vary. In some embodiments, either device is located at an end of the flexible support element. The flexible support element and device may form a single, integrated piece. In other words, the spinal device or spinal fusion device may be an extension of the flexible support element. However, the flexible support element and the spinal device or spinal fusion device may be separate pieces, connected and attached to at least one common vertebra by any of the connectors disclosed above. In other embodiments, the spinal device or spinal fusion device is located under or over the flexible support element. Again, the flexible support element and either device may form a single, integrated piece, or may be separate pieces, connected and attached to at least one common vertebra.

Also disclosed are methods for using the apparatuses disclosed herein. The methods comprise implanting into a subject any of the apparatuses disclosed herein. Any subject in need of the apparatuses may be used, including, but not limited to human subjects. The apparatuses may be used in the cervical, thoracic and lumbar regions of the spine and may be implanted by an open procedure, endoscopically or laprascopically. Such implantation techniques are known.

The following figures show examples of apparatuses according to the present invention. The embodiments shown in the figures are intended only to exemplify the invention and should not be construed to limit the invention to any particular embodiment. The drawings are not necessarily to scale and the relative dimensions of the components of the apparatuses provided therein may deviate from those shown in the figures.

FIG. 1 shows a posterior view of adjacent vertebrae 100 and 104. Although the intervertebral disc is not shown, the vertebrae are not fused to each other. They may, however, be fused to other vertebrae. The apparatus includes a flexible support element 108 attached to both vertebrae with connectors 112. The flexible support element spans the intervertebral space 116. The inset in the figure shows the mesh-type structure 118 of the flexible support element. The mesh-type structure includes both vertical 120 and horizontal components 122. However, as described above, the flexible support element may assume other forms. The apparatus also includes two compartments 124. These compartments include bone growth promoter 126 for anchoring the flexible support element to each of the vertebrae. However, the bone growth promoter does not span the intervertebral disc space and thus, will not facilitate the growth of bone between the vertebrae 100 and 104. Although the apparatus of FIG. 1 spans one intervertebral space, the flexible support element may be long enough to attach to other vertebrae and to span more than one intervertebral space. In other words, multi-level flexible support elements are possible.

Figure 2:
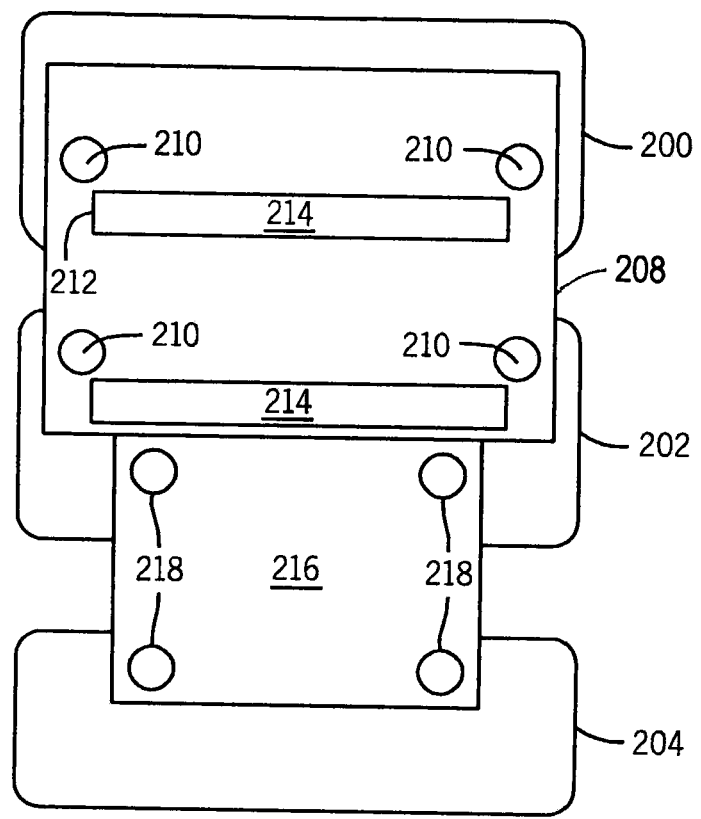
FIG. 2 shows the apparatus of FIG. 1 with a spinal fusion device coupled to the flexible support element.

FIG. 2 shows a posterior view of three vertebrae 200, 202, and 204. The apparatus includes a flexible support element 208, connectors 210, and compartments 212 including bone growth promoter 214. The flexible support element may or may not comprise a mesh-type structure. The apparatus further includes a spinal fusion device 216 positioned at an end of the flexible support element. The spinal fusion device is attached to vertebrae 202 and 204 via connectors 218. In this case, the vertebrae 202 and 204 are fused to each other.

Although the apparatus of FIG. 2 shows only one flexible support element, another flexible support element may be positioned below the spinal fusion device 216. Such a flexible support element would be attached at least to vertebra 204 and a vertebra (not shown) below vertebra 204.

Figure 3:
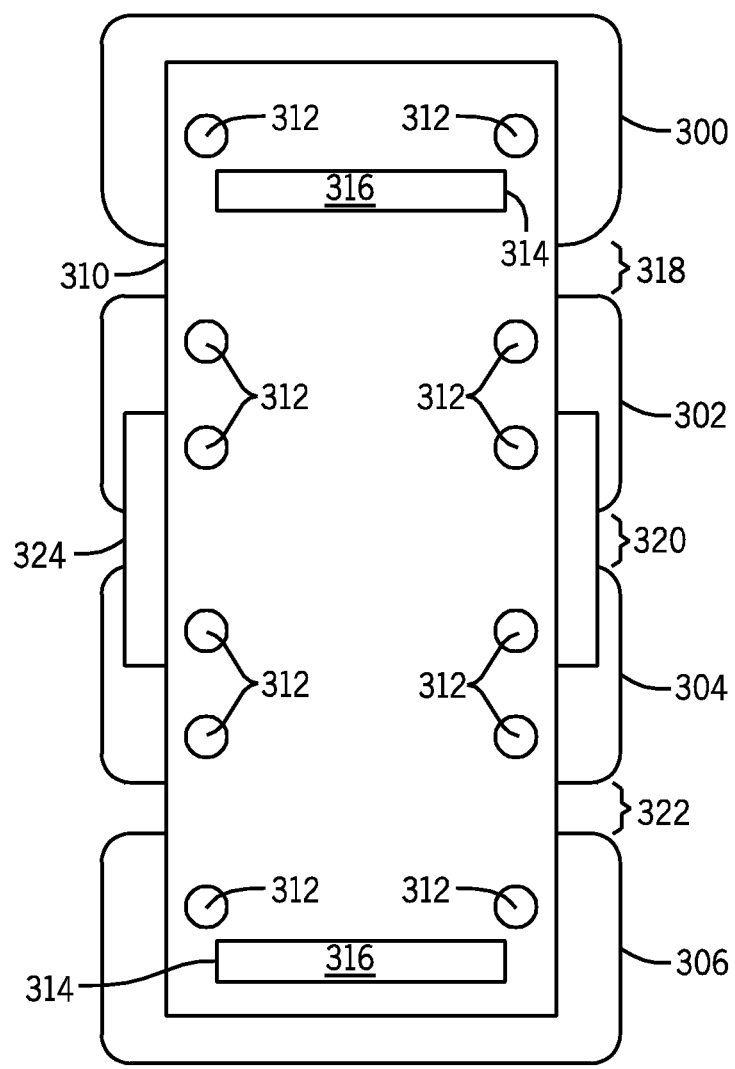
FIG. 3 shows an apparatus including a multi-level flexible support element attached to four vertebrae. Compartments including bone growth promoter are coupled to the flexible support element. In addition, the apparatus includes a spinal fusion device coupled to and positioned underneath, the flexible support element.

FIG. 3 shows a posterior view of four vertebrae 300, 302, 304, and 306. The apparatus includes a flexible support element 310, connectors 312, and compartments 314 including bone growth promoter 316. The flexible support element is multi-level, spanning three intervertebral spaces 318, 320, and 322. The flexible support element may or may not comprise a mesh-type structure. The apparatus further includes a spinal fusion device 324. In this case, the spinal fusion device is positioned underneath the flexible support element 310 and shares a number of the connectors 312 with the flexible support element. Vertebrae 302 and 304 are fused to each other. Thus, vertebrae 302 and 304 are fused vertebrae. However, vertebrae 300 is not fused to vertebra 302 and vertebra 306 is not fused to vertebra 304. Vertebrae 300 and 306 may, however, be fused to other vertebrae.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

For the purposes of this disclosure and unless otherwise specified, "a" or "an" means "one or more." All patents, applications, references and publications cited herein are incorporated by reference in their entirety to the same extent as if they were individually incorporated by reference.

While some detailed embodiments have been illustrated and described, it should be understood that such detailed embodiments are merely exemplary and changes and modifications cm be made therein in accordance with ordinary skill in the art without departing from the invention in its broader aspects as defined in the following claims.

What is claimed is:

1. An apparatus comprising: a flexible support;
   a first and second connector extending through the flexible support element and configured to attach to a first vertebra when installed;
   a third connector extending through the flexible support element and configured to attach to a second vertebra when installed;
   a spinal fusion device coupled to the flexible support element and configured to be coupled to one of the first vertebra and the second vertebra, and configured to be coupled to a third vertebra that is adjacent to the one of the first vertebra and the second vertebra;
   a first compartment on the flexible support element proximate the first vertebra and independent of and separate from the connectors, wherein the first compartment spans a distance between the first and second connectors;
   a second compartment on the flexible support element proximate the second vertebra and independent of and separate from the connectors;
   and a bone growth promoter disposed in the compartments,
   wherein the flexible support element spans one or more intervertebral spaces but the compartments and the bone growth promoter do not span the one or more intervertebral spaces, so that a growth of bone between the one or more intervertebral spaces is avoided.

2. The apparatus of claim 1, wherein the flexible support element comprises a biocompatible material selected from the group consisting of a memory metal alloy, titanium, a titanium alloy, cobalt chrome, a cobalt chrome alloy, a ceramic, stainless steel, and a polymer.

3. The apparatus of claim 1, wherein the flexible support element comprises a perforated plate.

4. The apparatus of claim 3, wherein the perforated plate comprises a mesh-type structure.

5. The apparatus of claim 4, wherein the mesh-type structure does not comprise a diagonal component.

6. The apparatus of claim 1, wherein the bone growth promoter is selected from bone, demineralized bone matrix, mineralizing proteins, ossifying proteins, bone morphogenetic protein, hydroxyapatite, or hydroxyapatite tricalcium phosphate.

7. The apparatus of claim 1, wherein the bone growth promoter comprises bone morphogenetic protein.

8. The apparatus of claim 1, wherein the flexible support element is coated or impregnated with the bone growth promoter.

9. The apparatus of claim 1, wherein the compartments comprise a sponge and the sponge comprises the bone growth promoter.

10. The apparatus of claim 1 wherein the bone growth promoter is an electrical stimulator.

11. The apparatus of claim 1, wherein the first vertebra and second vertebra are non-fused vertebrae.

12. The apparatus of claim 1, wherein the spinal fusion device is configured to fuse the first vertebra and the second vertebra.

13. The apparatus of claim 1, wherein the spinal fusion device and the flexible support element are formed as a single, integrated piece.

14. The apparatus of claim 1 wherein the spinal fusion device is positioned under or over a portion of the flexible support element.

15. An apparatus comprising: a flexible support element;
   a first and second connector extending through the flexible support element and configured to attach to a first vertebra when installed;
   a third connector extending through the flexible support element and configured to attach to a second vertebra when installed;
   a spinal fusion device positioned proximate one end of the flexible support element and configured to be coupled to one of the first vertebra and the second vertebra, and configured to be coupled to a third vertebra that is adjacent to the one of the first vertebra and the second vertebra;
   said connectors configured to couple the flexible support member to the first vertebra and the second vertebra;

a first compartment on the flexible support element proximate the first vertebra and independent of and separate from the connectors wherein the first compartment spans a distance between the first and second connectors;
a second compartment on the flexible support element proximate the second vertebra and independent of and separate from the connectors;
a bone growth promoter disposed within the first compartment and the second compartment,
wherein the flexible support element spans one or more intervertebral spaces but the compartments and the bone growth promoter do not span the one or more intervertebral spaces, so that a growth of bone between the one or more intervertebral spaces is avoided.

16. The apparatus of claim 15, wherein the spinal fusion device and the flexible support element are formed as a single, integrated piece.

* * * * *